United States Patent [19]

Williams

[11] Plant 4,579

[45] Jul. 29, 1980

[54] MINIATURE ROSE PLANT

[76] Inventor: Ernest D. Williams, 1510 Lebanon Ave., Dallas, Tex. 75208

[21] Appl. No.: 29,142

[22] Filed: Apr. 11, 1979

[51] Int. Cl.[2] ..... A01H 5/00

[52] U.S. Cl. ..... Plt./7

[58] Field of Search ..... Plt./7

*Primary Examiner*—Robert E. Bagwill
*Assistant Examiner*—James R. Feyrer

[57] ABSTRACT

The subject of the present disclosure is a new and distinct variety of miniature rose plant characterized by the red (or pink) and white color combination of the buds and flowers and by the profusion of bloom.

1 Drawing Figure

The present invention relates to a new and distinct variety of hardy, dwarf, bush type rose plant of the miniature class; the variety being primarily characterized—as to novelty—by bi-color buds and flowers of shades of red (or pink) and white which in general color effect are similar to Magic Carrousel (miniature—U.S. Plant Pat. No. 3,601) but smaller in size.

The variety is further characterized by:

An abundance of bloom, with flowers usually borne singly, but sometimes several together in loose clusters.

A plant which is vigorous, of rounded somewhat upright shape with semi-glossy to matt, small foliage with pointed leaflets; the buds and flowers being similar in form and size to Kathy (miniature—U.S. Plant Pat. No. 3,246).

The plant, which has a normal height of 12–14 inches, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Dallas, Tex., under conditions of careful control and observation, as a cross between Little Darling, Floribunda (U.S. Plant Pat. No. 1,581, expired) as the seed parent and Little Chief (miniature—not patented), as the pollen parent.

Subsequent to origination of the variety I successfully reproduced it, at my nursery, located as aforesaid, by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature.

*Variety name.*—Dreamglo.

Flowers borne: Usually singly—sometimes several on slender wirey stems.

Quantity of Bloom: Abundant both outside and in greenhouse.

Bud:

*Peduncle.*—Medium length; slender but sturdy; erect; medium green, sometimes tinted bronze (outdoors); Hairs — some.

*Before calyx breaks.*—Size — small. Form long; pointed with several foliaceous apendages and numerous tiny hairs on surface of bud; with foliaceous parts extending beyond the tip of the bud equal to one-half or less of its length. Color — medium greén, occasionally tinted with bronze (outdoors).

*As calyx breaks.*—Color — near white, often tinted pink near the tip. Opening: opens well in all weather.

Bloom:

*Size when fully open.*—Small, averaging about 1" or less in diameter.

*Petalage.*—Double — averaging about 50 petals, arranged regularly plus sometimes several small petaloids.

*Form.*—Pointed at first, becoming high centered as flower opens, with petals reflexing loosely outward and later at maturity, open and rolled loosely outward and downward. Open flowers may show some stamens.

Petals: Fairly thick; satiny on inside and on outside surface.

*Shape.*—Outside petals, broad lanceolate with rounded tip plus very small (short) acute tip; intermediate — broad lanceolate with tip similar to outside petal; inside — lanceolate with rounded or acute tip.

Color: Newly opened flower from plant grown outdoors at Dallas, Tex. and at Visalia, Calif.

*Outside petal.*—Outside surface — white or near-white shading or blending into soft pink (near Geranium Lake 20/3 or lighter) near tip. Inside surface — white or near-white, edged or blended at tip with red near or similar to Crimson 22.

*Intermediate petal.*—Outside surface — similar to outside petal. Inside surface — similar to outside petal.

*Inner petal.*—Outside surface — same as intermediate petal; inside surface — same as intermediate petal. General color effect; newly opened flowers — bright red (or deep pink) interspersed with white areas. Three days open — color similar to newly opened flowers but less brilliant. Behavior — opens well in all weather. Color lasts well on plant or in vase. Spent petals drop off. Flower longevity (Fall 1978) — plant in pot 6–8 days or longer. Cut flowers at living room temperature 4–5 days or longer.

Reproductive organs:

*Stamens.*—Few to moderate number, arranged regularly about pistils.

*Filaments.*—Varying length, fairly short, yellow.

*Anthers.*—Well formed yellow.

*Pollen.*—None to moderate amount.

*Pistils.*—Average number.

*Styles.*—Fairly even; medium to short length; bunched; color — reddish.

*Stigmas.*—Pinkish.

*Ovaries.*—All enclosed in calyx.

*Hips.*—None.

*Sepals.*—Permanent; spear shaped; recurved.

*Seed.*—None.

Foliage:

*Leaves.*—Compound of five (sometimes three or seven) leaflets; fairly small; leathery; semi-glossy to matt.

*Leaflets.*—Shape: broad, nearly oval; apex acute; base rounded or rounded acute. Margin serrate. Color: medium to dark green; new growth — normal green, often tinted bronze. Rachis: medium strength; upper side may have a few tiny short prickles or hairs, grooved; underside sparsely thorny with few or no tiny prickles. Stipules: medium long; narrow width; medium length; narrow points which turn out usually at about 45 degrees.

Growth:

*Habit.*—Dwarf; bushy; rounded; much branched.

*Growth.*—Free vigorous; internodes short.

*Canes.*—Medium; slender; sturdy.

*Main stems.*—Color: medium green.

*Thorns.*—Few to average; slender; color; brown. Prickles — none. Hairs — none.

*Branches.*—Color: medium green. Thorns: moderate number; medium length; slender; nearly straight. Medium oval base. Prickles: none. Hairs: none.

The miniature rose plant and its flowers as herein described may vary in slight detail due to climatic, soil and cultural conditions under which the variety may be grown; the present description being of the variety as grown at Dallas, Tex., and Visalia, Calif.

The following is claimed:

1. A new and distinct variety of miniature rose plant of hardy, dwarf, bush, rounded, much branched, habit, substantially as illustrated and described, characterized by buds and flowers of a red and white bi-color, with the red coloring on top side of petal, being of a shade generally near Crimson 22 or lighter, the bud and flower resembling the variety Magic Carrousel (U.S. Plant Pat. No. 3,601) in form and color but being generally smaller in size; and further characterized by a plant of vigorous and compact growth habit, easy to propagate from cuttings, with an abundance of flowers borne singly and sometimes several together.

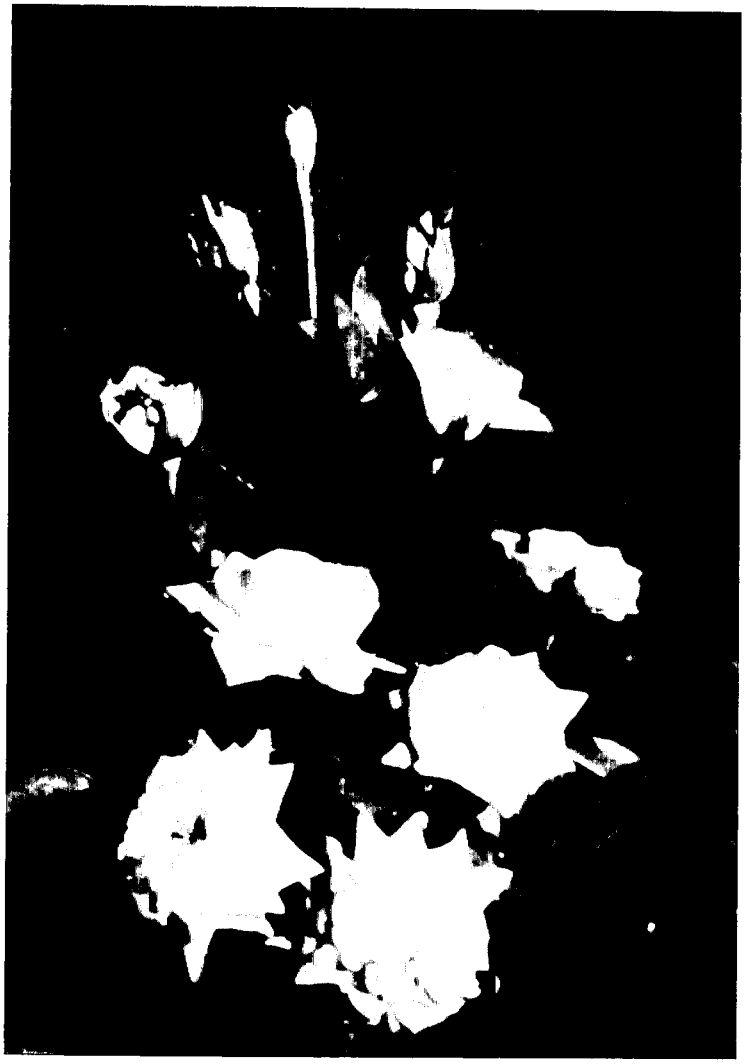

* * * * *